(12) United States Patent
Bonutti et al.

(10) Patent No.: US 6,203,565 B1
(45) Date of Patent: *Mar. 20, 2001

(54) SURGICAL DEVICES ASSEMBLED USING HEAT BONDABLE MATERIALS

(76) Inventors: Peter M. Bonutti, 1303 W. Evergreen Plaza; Mark V. Brillhart, 1108 Diana Ct., both of Effingham, IL (US) 62401

( * ) Notice: Subject to any disclaimer, the term of this patent is extended or adjusted under 35 U.S.C. 154(b) by 0 days.

This patent is subject to a terminal disclaimer.

(21) Appl. No.: 09/362,279

(22) Filed: Jul. 27, 1999

Related U.S. Application Data

(63) Continuation of application No. 08/929,168, filed on Sep. 12, 1997, now Pat. No. 5,941,900, and a continuation of application No. 09/267,555, filed on Mar. 12, 1999, now Pat. No. 6,059,817, which is a division of application No. 09/019,511, filed on Feb. 5, 1998, now Pat. No. 5,928,267, which is a division of application No. 08/782,595, filed on Jan. 13, 1997, now Pat. No. 5,735,875, which is a division of application No. 08/453,631, filed on May 30, 1995, now Pat. No. 5,593,425, which is a continuation-in-part of application No. 07/833,085, filed on Feb. 10, 1992, now abandoned, which is a division of application No. 07/545,919, filed on Jun. 28, 1990, now Pat. No. 5,163,960.

(51) Int. Cl.[7] .................................................. A61B 17/04
(52) U.S. Cl. ........................ 606/232; 606/215; 606/220; 606/228
(58) Field of Search .................................. 606/232, 220, 606/228, 215

(56) References Cited

U.S. PATENT DOCUMENTS

| | | |
|---|---|---|
| 3,513,848 | 5/1970 | Winston et al. . |
| 4,064,566 | 12/1977 | Fletcher et al. . |
| 4,171,544 | 10/1979 | Hench et al. . |
| 4,200,939 | 5/1980 | Oser . |
| 4,351,069 | 9/1982 | Ballintyn et al. . |
| 4,414,166 | 11/1983 | Charlson et al. . |
| 4,456,005 | 6/1984 | Lichty . |
| 4,506,681 | 3/1985 | Mundell . |
| 4,547,327 | 10/1985 | Bruins et al. . |
| 4,645,503 | 2/1987 | Lin et al. . |
| 4,662,068 | 5/1987 | Polonsky . |
| 4,669,473 | * 6/1987 | Richards et al. ..................... 606/215 |
| 4,718,909 | 1/1988 | Brown . |
| 4,750,492 | 6/1988 | Jacobs . |
| 4,792,336 | 12/1988 | Hlavacek et al. . |
| 4,832,025 | 5/1989 | Coates . |

(List continued on next page.)

OTHER PUBLICATIONS

Advertising brochure entitled "Why tie a Knot when you can use Y–Knot?", publication date ;unknown, copyright 1998 Innovasive Devices Inc.

*Primary Examiner*—Gary Jackson
(74) *Attorney, Agent, or Firm*—Tarolli, Sundheim, Covell, Tummino & Szabo, L.L.P.

(57) ABSTRACT

Surgical devices such as implants or suture fastenings are assembled from a plurality of discrete components, one of which components includes a heat bondable plastic material for bonding the components together. At least two components are bonded to each other by the applying heat to the heat bondable plastic material of one component. The heat bondable plastic material is preferably a polymeric or composite material suitable for surgical applications and implantation in humans, and may be a biodegradable material. A laser may be used as the heat source. The present invention is advantageously embodied in heat bonded fastenings for sutures or K-wires, in which a variety of different suture anchors are usable, including expandable distal suture anchors. Other embodiments include a metal bone plate which is held to bone by a metal bone screw and a nut of bondable material bonded to the plate to secure the connection; a piece of bondable material bonded to a metal prosthesis to custom fit the prosthesis; and a surgical implant custom formed by bonding together a plurality of discrete elements one or more of which is bondable.

73 Claims, 7 Drawing Sheets

U.S. PATENT DOCUMENTS

| | | |
|---|---|---|
| 4,935,028 | 6/1990 | Drews . |
| 5,098,433 | 3/1992 | Freedland . |
| 5,156,613 | 10/1992 | Sawyer . |
| 5,209,776 | 5/1993 | Bass et al. . |
| 5,254,113 | 10/1993 | Wilk . |
| 5,306,280 | 4/1994 | Bregen et al. . |
| 5,370,646 | 12/1994 | Reese et al. . |
| 5,474,554 | 12/1995 | Ku . |
| 5,531,759 | 7/1996 | Kensey et al. . |
| 5,593,422 | 1/1997 | Van De Moer et al. . |
| 5,620,461 | 4/1997 | Van De Moer et al. . |
| 5,643,295 | 7/1997 | Yoon . |
| 5,810,884 | 9/1998 | Kim . |

\* cited by examiner

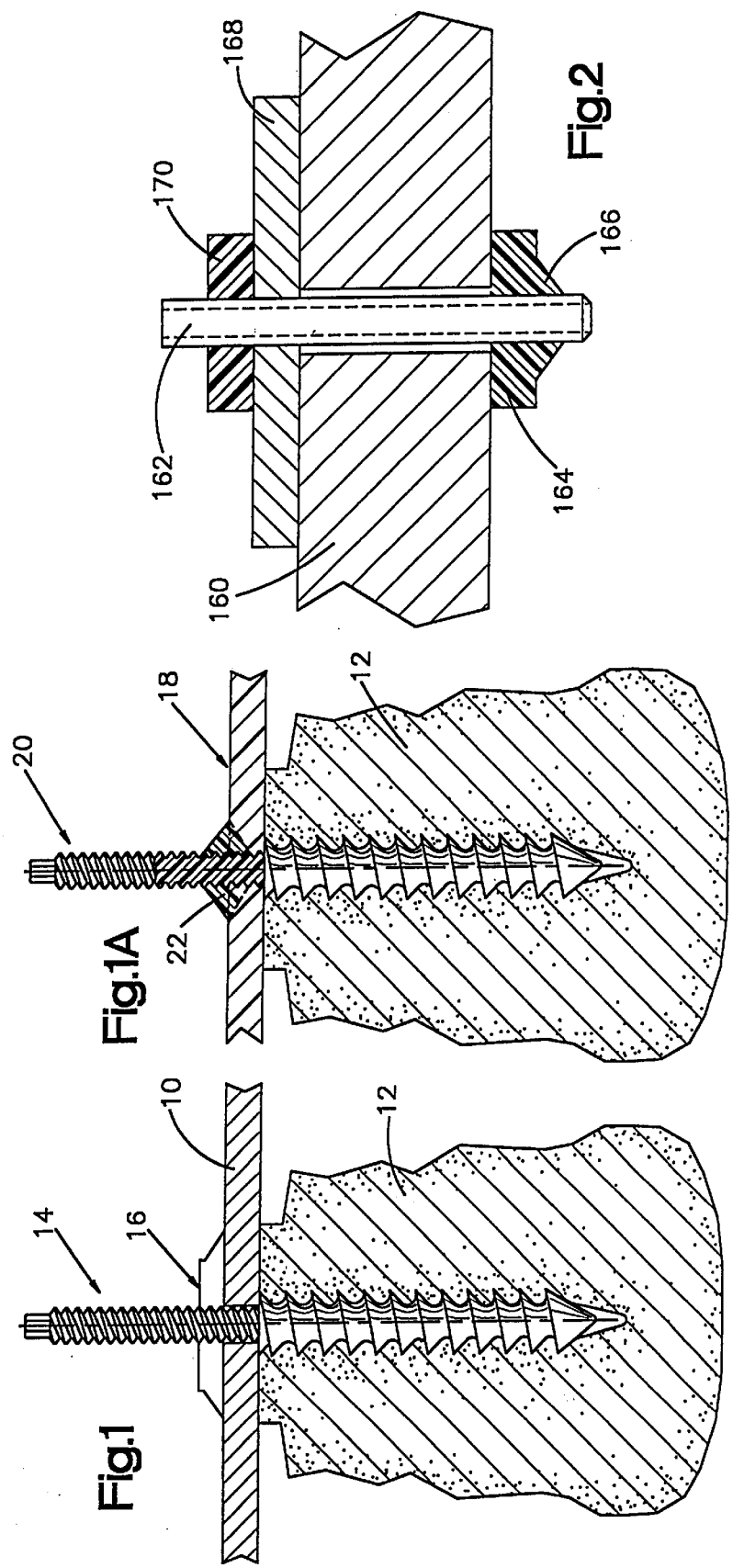

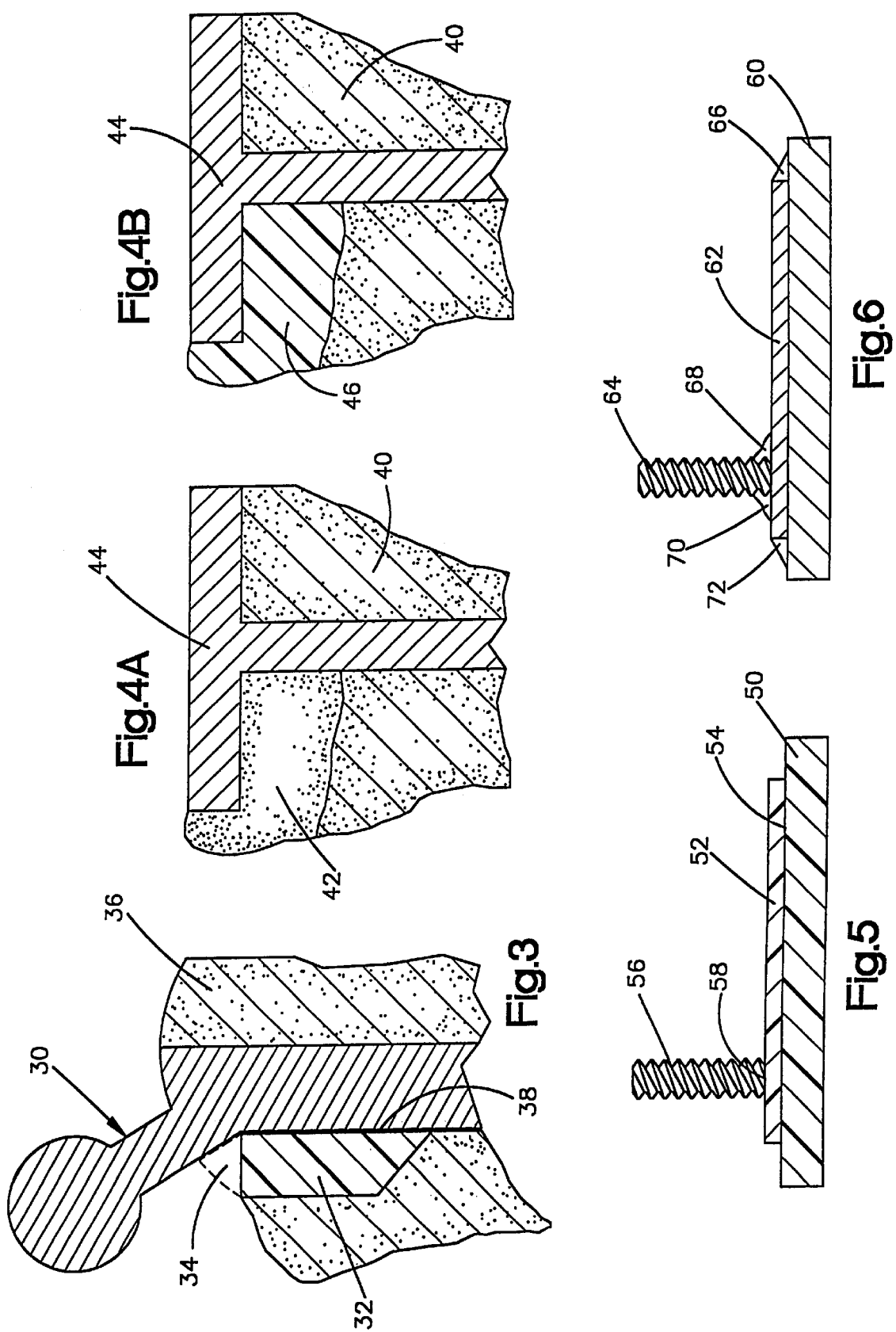

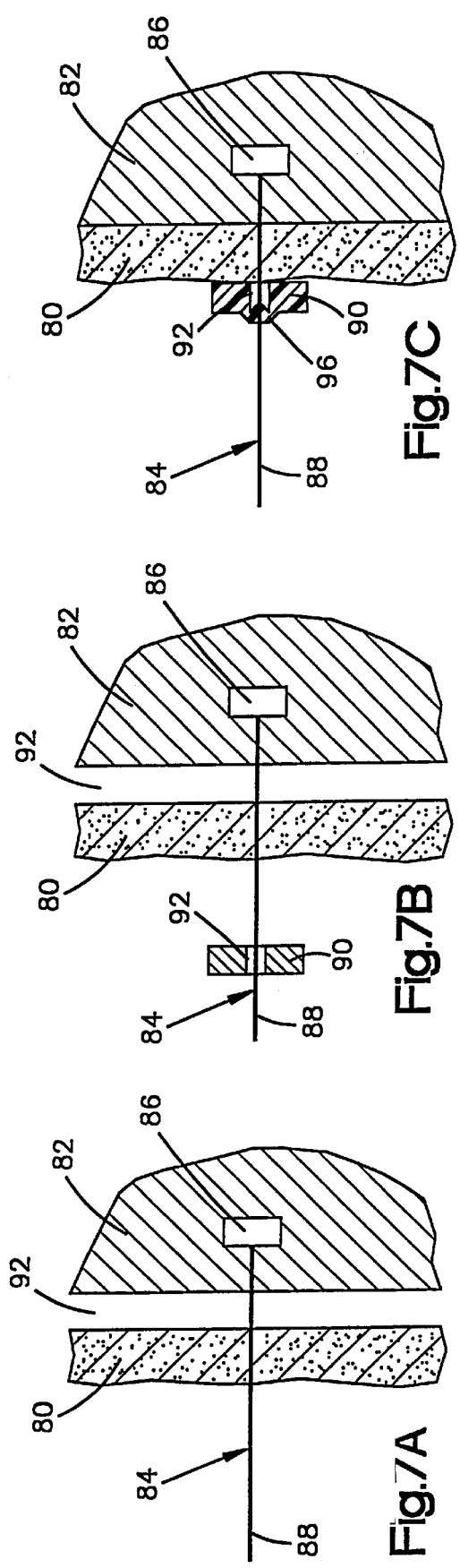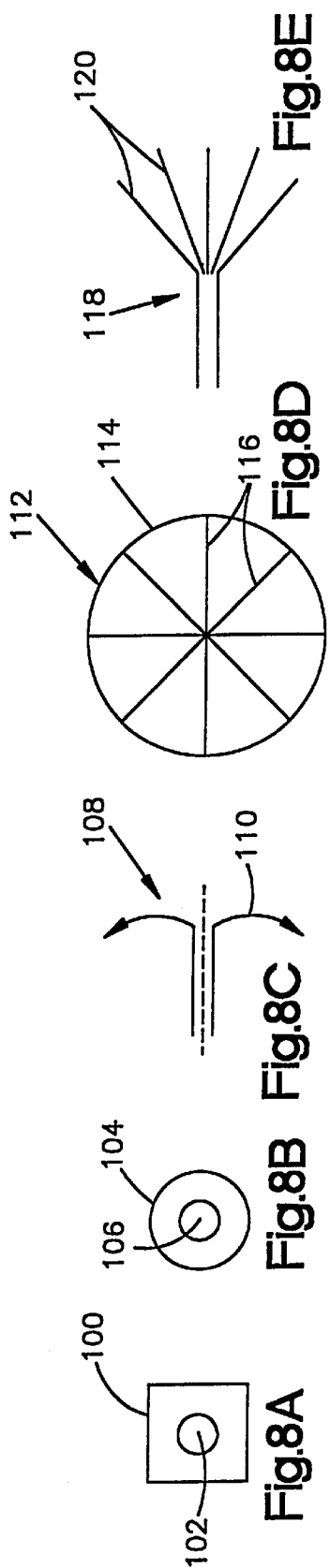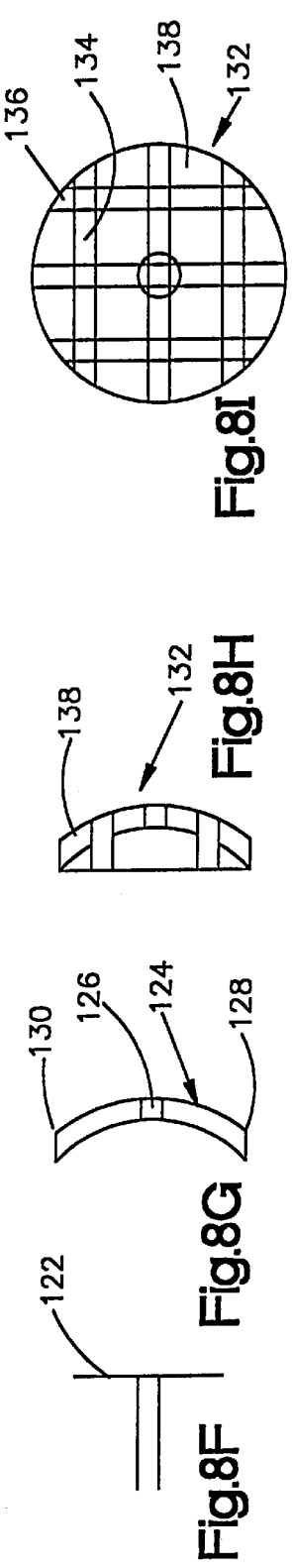

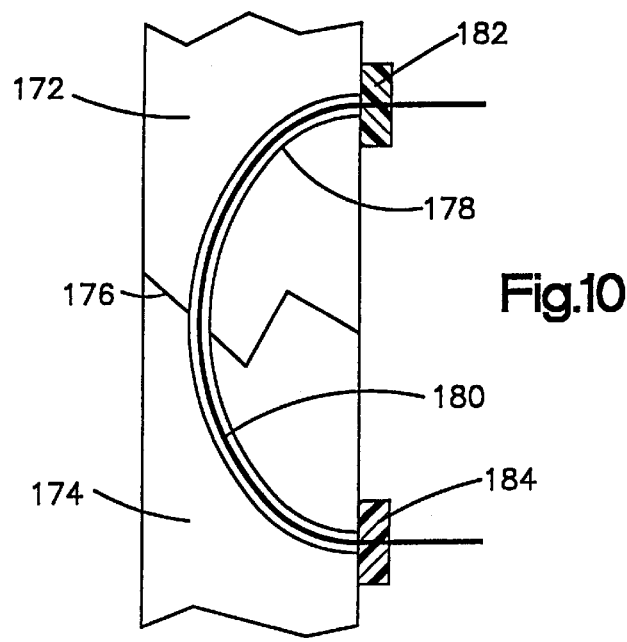
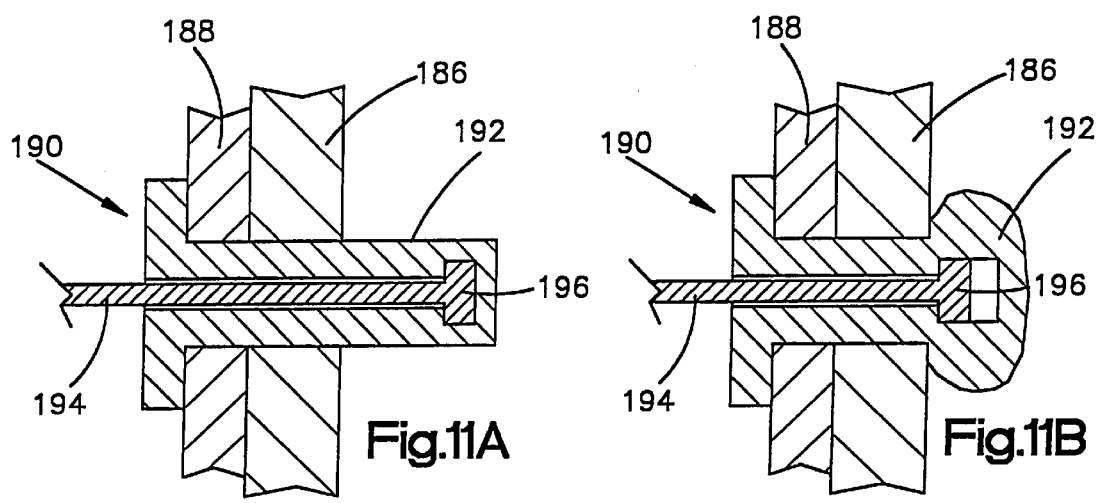
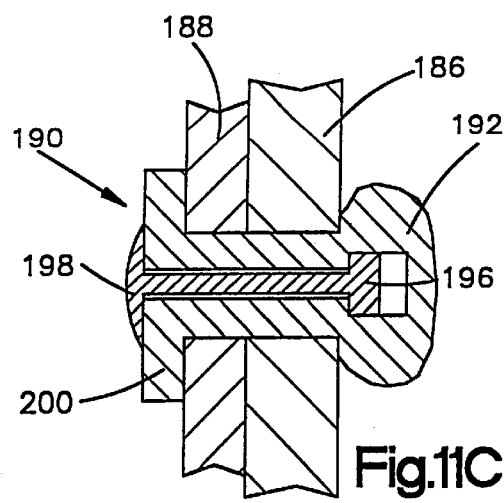

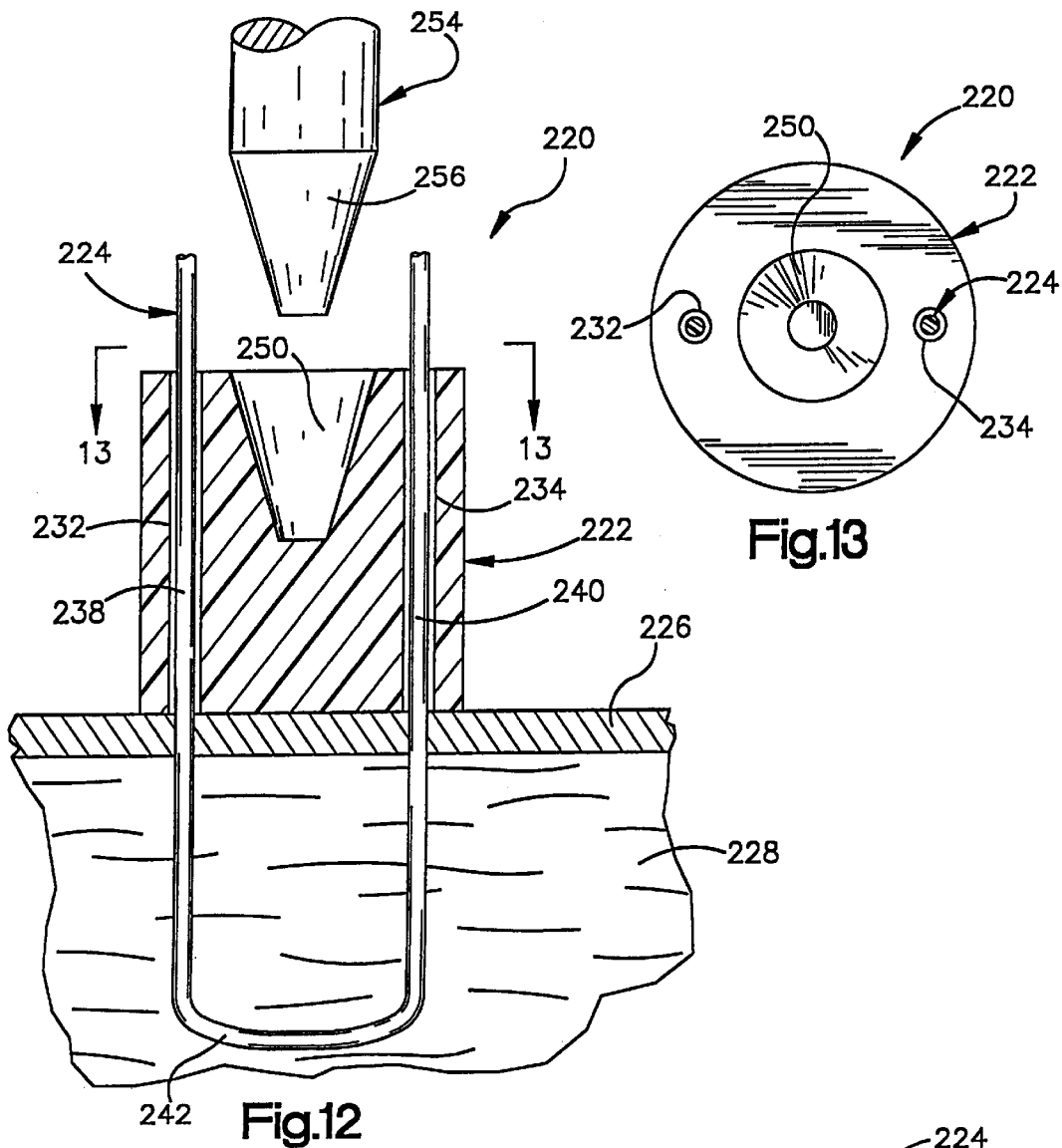
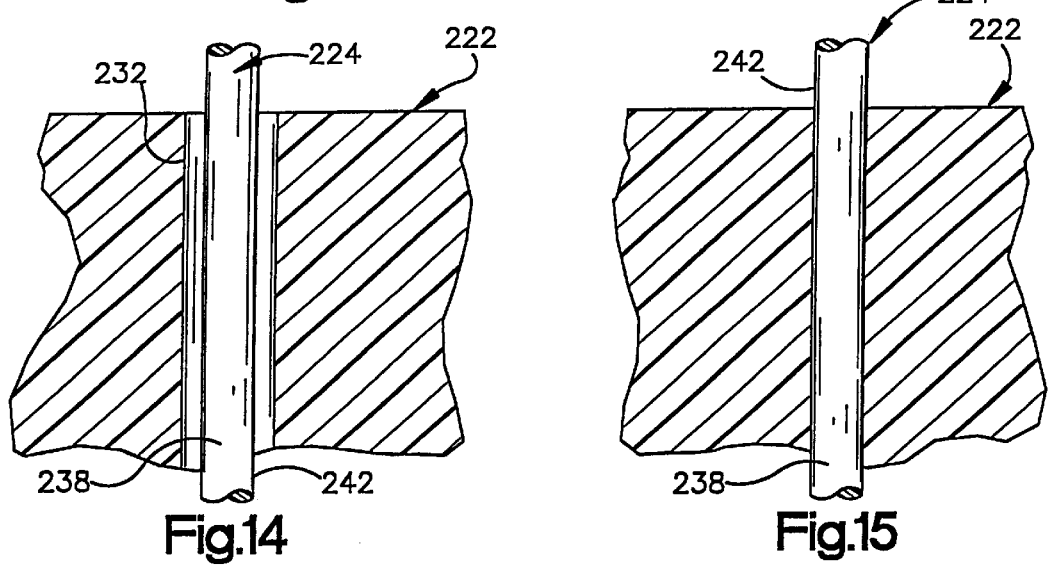
Fig.12  Fig.13  Fig.14  Fig.15

SURGICAL DEVICES ASSEMBLED USING HEAT BONDABLE MATERIALS

RELATED APPLICATIONS

This application is a continuation of Ser. No. 08/929,168, filed Sep. 12, 1997, now U.S. Pat. No. 5,941,900. This application is a continuation of application Ser. No. 09/267,555, filed Mar. 12, 1999 now U.S. Pat. No. 6,059,817 and entitled "Surgical Devices Assembled Using Heat Bondable Materials". The aforementioned Ser. No. 09/267,555 is itself a divisional application Ser. No. 09/019,511 filed Feb. 5, 1998 U.S. Pat. No. 5,928,267. The aforementioned application Ser. No. 09/019,511 is itself a divisional of application Ser. No. 08/782,595 filed Jan. 13, 1997, now U.S. Pat. No. 5,735,875. The aforementioned application Ser. No. 08/782,595 is itself a divisional of application Ser. No. 08/453,631 filed May 30, 1995, now U.S. Pat. No. 5,593,425. The aforementioned application Ser. No. 08/453,631 is itself continuation-in-part of application Ser. No. 07/833,085 filed Feb. 10, 1992, now abandoned. The aforementioned application Ser. No. 07/833,085 is itself a divisional of Ser. No. 07/545,919 filed Jun. 28, 1990, and now U.S. Pat. No. 5,163,960. The benefit of the earlier filing dates of the aforementioned applications is hereby claimed.

BACKGROUND OF THE INVENTION

1. Technical Field

The present invention relates to surgical devices such as implants or suture fastenings.

2. Description of the Prior Art

Mundell U.S. Pat. No. 4,506,681 shows the use of a prosthesis which includes a biodegradable thermoplastic material molded around electric resistance elements to allow for heating to soften to mold to a particular shape.

Polonsky U.S. Pat. No. 4,662,068 discloses cutting off most of the protruding ends of a plastic suture and heating them to secure the ends together.

Jacobs U.S. Pat. No. 4,750,492 shows crimping or clipping a biodegradable fastener or retainer on the end of a biodegradable suture.

The compound methyl methacrylate is an acrylic resin monomer which is sometimes used in surgery to fasten or grout implants of metal to bone, or hip or knee replacements to bone. It is usable only for bone to metal applications. Tissue reacts to it and in soft tissue it creates a fibrous scar. Further, it is not biodegradable.

SUMMARY OF THE INVENTION

The present invention includes an assembly for use in surgical applications in humans. The assembly may include two components, at least one of which comprises a heat bondable material. The first and second components are bond to each other by the application of heat to the heat bondable material, to make the heat bondable material soften, become tacky, and bond to the other component.

If only one of the components comprises a heat bondable material, the application of heat to the heat bondable material of that component causes the heat bondable material to soften and bond to the other component.

If both of the components comprise a heat bondable material, the application of heat to the heat bondable material of the components causes the heat bondable material of at least one and preferably each component to soften and bond to the other component.

The assembly can also include a first component, a second component, and a third component separate from the first and second components and comprising a heat bondable material. The application of heat to the heat bondable material of the third component causes the heat bondable material to soften and bond to the first and second components to interconnect the first and second components.

The heat bondable material is preferably a polymeric or composite material suitable for surgical applications and implantations in humans, and may be a biodegradable material where such is called for by the application.

The present invention may advantageously be embodied in heat bonded fastenings for sutures or K-wires, in which a variety of different suture anchors are usable, including expandable distal suture anchors. Such suture fastenings are easier to form and stronger than conventional tied knots. Other examples of assemblies embodying the present invention may include a metal bone plate which is held to bone by a metal bone screw and a nut of bondable material bonded to the plate to secure the connection; a wedge of bondable material bonded to a metal prosthesis to custom fit the prosthesis; and a surgical implant custom formed by bonding together a plurality of discrete elements one or more of which is bondable. Such embodiments are further described below.

The present invention may also provide a method of suturing body tissue. A portion of a suture is inserted into an opening in a retainer formed of a plastic material. At least a portion of the retainer is heated to a temperature in a transition temperature range of the plastic material forming the retainer. The suture is maintained at a temperature below the transition temperature range of a plastic material forming the suture while the retainer is heated. The plastic material of the retainer flows around the plastic material of the suture. A bonding of the plastic material of the retainer to the plastic material of the suture is effected by cooling the plastic material of the retainer to a temperature below its transition temperature range. The foregoing steps are performed without significant deformation of the plastic material of the suture.

BRIEF DESCRIPTION OF THE DRAWINGS

Further features of the present invention will become apparent to those skilled in the art to which the present invention relates from reading the following specification with reference to the accompanying drawings, in which:

FIG. 1 is an illustration of a metal bone plate which is held to bone by a metal bone screw and a nut of bondable material bonded to the plate to secure the connection in accordance with one of the features of the present invention;

FIG. 1A is an illustration of a bone plate of bondable material which is held to bone by a bone screw and nut both of bondable material and bonded to each other to secure the connection;

FIG. 2 illustrates the use of a bonded fastening in accordance with one of the features of the present invention to obtain increased holding power on a fastener extending through a bone;

FIG. 3 is an illustration of a wedge of bondable material bonded to a metal hip prosthesis to custom fit the prosthesis;

FIG. 4 is an illustration of a wedge of bondable material bonded to a metal tibial prosthesis to custom fit the prosthesis;

FIG. 5 is an illustration of a surgical implant custom formed by bonding together a plurality of discrete bondable elements;

FIG. 6 is an illustration of the use of a third component of bondable material to custom form a surgical implant by bonding together a plurality of discrete elements;

FIG. 7 is an illustration of a bonded suture fastening in accordance with one of the features of the present invention;

FIG. 8 is a schematic illustration of a variety of different suture anchors usable in bonded suture fastenings;

FIG. 10 illustrates the use of a curved hole in tissue parts to be joined with bonded fastenings on either end of the joining element;

FIG. 11 is an illustration of a bonded rivet in accordance with one of the features of the present invention;

FIG. 12 is a schematic sectional view illustrating the manner in which a suture is placed relative to body tissue and extends into openings in a retainer;

FIG. 13 is a plan view, taken generally along the line 13—13 of FIG. 12, further illustrating the construction of the retainer;

FIG. 14 is an enlarged fragmentary sectional view of a portion of FIG. 13;

FIG. 15 is an enlarged fragmentary sectional view, generally similar to FIG. 14, illustrating the manner in which the retainer is bonded to the suture without significant deformation of the suture;

DESCRIPTION OF PREFERRED EMBODIMENTS

Figure 9A:
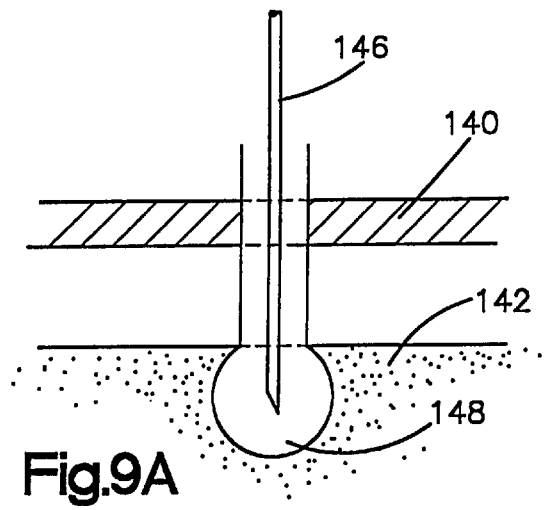
FIG. 9 is an illustration of an expandable distal suture anchor usable in bonded suture fastenings.
Figure 9B:
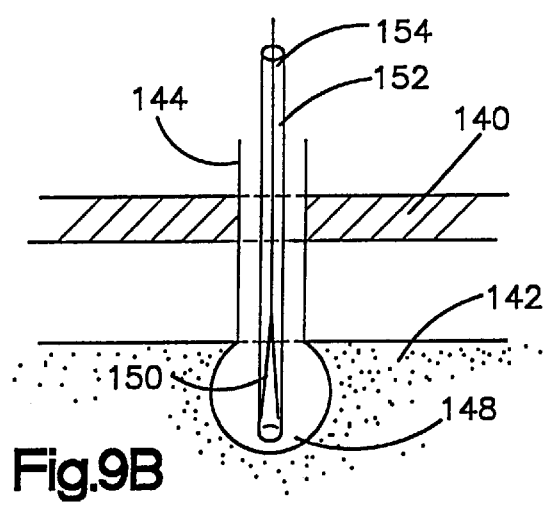
Figure 9C:
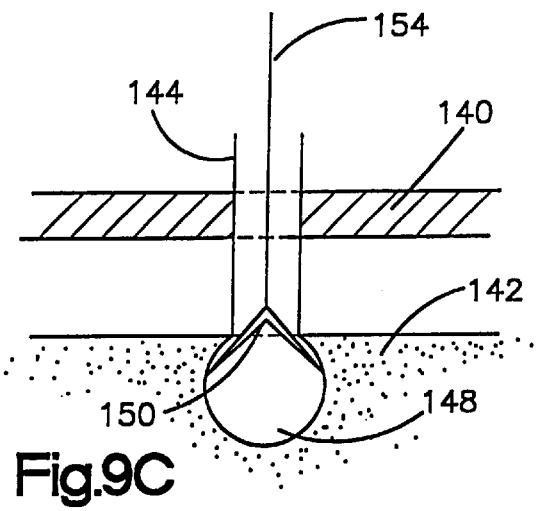

In this application, the term "bondable" or "bondable material" is used to refer to any material, suitable for use in surgical applications, which can be softened and made flowable by the application of heat, and which, when softened, will become tacky and bond to other materials and will flow to fill available space. Thus, the material may be thermoplastic, but it may also exhibit tackiness or bonding ability when in its plastic form. Many materials suitable for surgery are made of or incorporate such heat bondable materials. Many biodegradables, polymers such as polyethylene, and composites fall in this class. They can be joined by heat bonding at reasonably low temperatures which can be applied in the operating room safely, unlike the very high temperatures needed to melt metal. Composite materials can include reinforced plastics, or polymers which are laminated or layered or reinforced with one or more other materials such as nylon, graphite fibers, Kevlar® fibers, stainless steel fibers, etc. Many sutures are made of polymers which are suitable for use herein. Selection of such material is within the ordinary skill of the art.

Various components of at least some embodiments of the invention are formed of a plastic material. A plastic material is a material which contains one or more polymers and which may also contain other materials such as fillers, solvents, plasticizers, lubricants, accelerators, dyes, etc. An interconnection or bond between plastic materials occurs as a result of molecular attraction (adhesion) and/or mechanical force resulting from shrinking of the plastic material. A transition temperature range of the plastic material is a temperature range at which the plastic material changes from a solid condition in which it has a fixed form to a viscous condition in which the material readily flows and is soft enough to be molded.

Any suitable heat generating apparatus can be used to heat and soften or spot weld the material, such as a hot air gun, a small welding or soldering gun, or a Bovie tip. Also usable are lasers, which are commonly provided in operating rooms. Lasers are especially desirable because they are precise and controlled in their application, can generate sufficient heat very quickly, and cause less thermal necrosis because there is less misdirected heat. The heating operation can be done pre-operatively to form an assembly; can be done outside the body but in the operating room to customize implants at the time of surgery; or can be done during surgery, in the body, when the bond is needed within the human body.

First Embodiment

FIGS. 1 and 2 illustrate heat bonded assemblies including existing surgical objects such as plates, screws, etc. In FIG. 1, a bone plate 10 is secured to bone material 12 by a bone screw 14. The bone plate 10 and the bone screw 14 are both made of metal. Ordinarily, the bone screw 14 would be secured to the bone plate 10 by a metal nut threaded onto the bone screw 14 and run up adjacent the bone plate 10. However, such a connection can loosen and thus destroy the integrity of the assembly. Accordingly, in accordance with the present invention, a nut 16 is provided which is made of or includes a bondable material. The nut 16 is threaded on the bone screw 14 into abutting engagement with the bone plate 10. Then, the bondable material of the nut 16 is heated and softened to flow about the joint between the nut 16 and the bone plate 10, to bond the nut 16 to the bone plate 10. The nut 16 can also be bond to the bone screw 14 if desired for a stronger connection.

FIG. 1A illustrates an assembly similar to FIG. 1 in which a bone plate 18 and a bone screw 20 both made of or including bondable material are provided. The nut 16 (FIG. 1) is not used. Instead, the bone screw 20 is bonded directly to the bone plate 18 at an area 22.

As noted, ordinarily a bone plate is held to bone via a threaded fastener such as the bone screw 14 or 20 in FIG. 1. However, the bone is alive and is constantly remodeling the threads on the bone screw. As this happens, the fastener loses its purchase or holding power in the bone, and the screw can pull loose. Accordingly, it would be desirable to obtain more purchase by a different kind of fastener.

FIG. 2 illustrates the use of a bonded fastening in accordance with the present invention to obtain increased holding power. The fastener extends completely through a tissue mass such as a bone 160, for example to secure a plate in position against the bone. An elongate fastener 162, which may be metal or may be made of or include a bondable material, is inserted through an opening in the bone 160. A distal fastener 164 is secured to the distal end of the screw 162 by a plug of bonded material 166. The plate 168 is then placed over the bone screw, and a proximal fastener 170 made of or including a bondable material is bonded to either or both of the screw 162 and the plate 168. The elongate fastener 162 may optionally also be threaded in the portion engaging the bone 160. The elongate fastener 162 may optionally also be threaded in the portion engaging the fastener 164 and/or the fastener 170.

The bonded fastenings obtained thereby are stronger than is possible with either a threaded connection or a tied or crimped connection. Further, there is no reliance on a threaded connection between bone and fastener which will inevitably weaken over time. Also, bone screws are threaded and are always straight. The elongate fastener 162 need not be straight because it need not be threaded. Thus, it can be curved, or angled, as needed or desired to fit any particular application. In combination with the bonded connection of the fasteners at the ends of the elongate fastener, such a structure is a vast improvement over a typical metal threaded fastener.

FIGS. 3 and 4 illustrate surgical assemblies in which an existing surgical prosthesis or implant has been modified to better fit the particular application. Such prostheses or implants come from a manufacturer in only a limited range of sizes and shapes. However, the particular bone into which a prosthesis or implant is to be inserted may have defects or size discrepancies which would make it impossible to obtain a good fit with even the closest fitting prosthesis or implant.

In accordance with one of the features of the invention, the shape and size of a prosthesis or implant are modified to fit a particular bone. A femoral prosthesis 30 illustrated in FIG. 3 has been modified with the addition of a wedge 32 including heat bondable material in order to better fit a gap 34 in the bone 36. The wedge 32 is custom shaped to fit the gap 34 exactly. The connection 38 between the wedge 32 and the prosthesis 30 is secured by heating and softening the wedge 32 so that the material of the wedge 32 adheres or bonds to the prosthesis 30. The assembly of the heat bondable wedge 32 and the femoral prosthesis 30 fits the femur 36 much more properly than would the prosthesis alone. This assembly can easily be made right in the operating room at the time of the joint reduction, allowing the surgeon to customize or equilibrate at the time of surgery.

Similarly, in FIG. 4, a tibia 40 is shown to have an area of defect 42 which makes it impossible to properly fit a tibial component 44. Accordingly, as seen in FIG. 4B, an element 46 including a heat bondable material is shaped with heat as by a laser in the operating room to fit the defect 42. The element 46 is then bonded to the tibial component 44 prior to placement thereof in the bone 40. The assembly of the tibial component 40 and the element 46 provides a proper fit in the tibia 40. There is no other suitable way of matching the requirements of bone and joint in the operating room.

The bone components shown in FIGS. 3 and 4 are only an illustration of the many kinds of objects which can be used to form assemblies embodying the present invention. It can thus be seen, as illustrated in FIGS. 3 and 4, that the present invention gives the surgeon the ability to immediately modify the shape and size of almost any existing surgical part including a prosthesis, in order to better fit the particular application for use in the body. This is accomplished by heat bonding a piece of bondable material onto the prosthesis, to make an assembly designed for the particular application. The piece can be custom shaped in the operating room to fit the application exactly by heating and bonding of a polymer or composite.

FIGS. 5 and 6 illustrate schematically some custom fabricated implants which can be constructed in accordance with the present invention. In FIG. 5, a relatively thick plate 50 is joined to a relatively thin plate 52. Both the plate 50 and the plate 52 are made of or include a bondable material. The plates 50 and 52 are joined at the area of the joint 54 between them, by bonding in accordance with the present invention. A third element such as a stud 56 may be added, with bonding at the joint 58 therebetween. Thus, the surgeon has the ability to laminate pieces in surgery and does not have to rely on pre-made hardware.

It should be understood that the illustration in FIG. 5 of plates and a stud is not limiting, but is only illustrative of the almost limitless number of surgical devices which can be constructed in accordance with the present invention. Items such as rods, bars, plates, or any type of construct usable in medical/surgical applications object can be custom shaped or built up in accordance with the present invention. They can be made of polymers or composites which can easily be cut with a laser and also softened to custom fit. They can be made of or include a biodegradable material in those instances where it is desired that the material be replaced, over time, with natural tissue ingrowth. They can also include tissue ingrowth promoters, antibiotics, or other additives as desired.

Rather than having one or both of the components to be joined made of a bondable material, a third component can be used to join them, with the third component being made of or including a heat bondable material. The third component is non-flowable and non-adherent at room temperature before use. When it is softened by heating and applied to the first and second components, it bonds to both components to interconnect them. A laser is ideal for heating the interpositional bonding material because of the accuracy available with the laser. As an example, FIG. 6 illustrates an assembly similar to FIG. 5 in which a plate 60 and a plate 62 and a stud 64 are joined by the use of additional bonding material at locations 66, 68, 70, and 72. In this case, the plates 60 and 62 and the stud 64 need not be made of heat bondable materials.

For example, a total hip or knee replacement is possible using components bonded together by heat. If some or all of the parts are made of heat bondable material such as polymers or composites, an assembly as described herein can be produced simply by the application of heat to bond the parts together as desired. If the replacement does not fit the existing bone exactly, it can be customized at the time of surgery by cutting as with a laser, by adding as by bonding, or by heating to bond wedges or pieces to it.

It can be seen that the present invention also provides the capability for forming a custom-fit surgical implant for bonding to a bone or to a bone prosthesis which comprises a component at least partially formed of a heat-bondable material which has been custom-shaped by the application of heat to said heat-bondable material. In this instance, the aforementioned laser is most suitable for forming the implant. The lasers which are commonly found in operating rooms can cut, shapes and otherwise form almost any suitable material used herein, including polymers, biodegradable materials, and even composites including reinforcing materials. The implant can include several components each having heat-bondable material, or several components only one of which includes a heat-bondable material, or it can be a single component which is custom made for a particular application. Such use of heat to form implants provides the surgeon with greatly extended capabilities in the operating room and does not limit him to pre-formed implants or prostheses.

Second Embodiment

It is difficult to tie a suture knot to itself or to slide it down through deep tissue in a limited working area (as in fiber optic surgery). Typically, the surgeon can often not work in a straight line but needs to use a suture loop (going through the tissue twice) to bring tissue together. Any such increase in the amount of tissue through which the suture must pass increases damage to tissue. Furthermore, mechanical tying or crimping of sutures or K-wires, especially of polymers or biodegradables which are generally smooth, does not produce connections which are as strong as desirable, and suture connections sometimes may come untied as a result.

In accordance with one of the features of the present invention, surgical connections for holding adjoining tissues together are secured by melting a fastener or anchor on the end of a suture, rather than by tying or by clipping the anchor on the end of the suture. (The term "suture" is used herein to refer to a suture, a K-wire, or any similar surgical connector.) The anchor is pushed over the free end of the suture down to the tissue, drawing the tissues together. Either the anchor alone or the anchor and the suture are melted together to lock them into position.

With the fasteners of the present invention, therefore, a surgeon has more control since he can apply more pressure to push the tissues together and it is easier to appose the tissues; the tension on the repaired tissues is more controllable, predictable, and reproducible; and the fasteners can be used in a smaller working space. Further, a melted anchor provides a stronger bond than the mechanical interlock of a suture knot, because it will not unravel or come apart as a surgical knot may. It takes less time to fasten than it does to tie a suitable knot. There is improved contact between the tissues being joined because of the better suture connection. The straight line suture fastening also avoids buckling of the tissue edges caused by force vectors not extending in the direction of the suture.

Since he only needs one free suture end to make a secure connection, the surgeon does not need to use a suture loop to bring tissue together, but can work in a straight line. This lessens damage to tissue because a straight line connection is easier to obtain than a loop in a limited space. Also, it improves tissue apposition and approximation when a straight line fastening is pulled together rather than a loop which tends to buckle or pucker tissue at the edges because of the force vectors not directed along the length of the suture.

The fasteners can be used for the fixation of soft tissue, tendon, ligament, meniscus, muscle, fascia, vessels, nerves or bones to each other. They can be used, for example, to hold a rotator cuff to bone, or to join fracture fragments of bone to bone. The anchors can be custom molded, specially made at the time of surgery (or preoperatively) to conform exactly to the tissue or bone application.

One anchor is secured to the distal end of the suture. (Alternatively, it may be preformed or connected on the suture in any known manner of connection.) The suture is then positioned in the tissues to be joined, a second anchor is slid over the free end, pulled down to close the gap, and melt it in place.

As illustrated in FIG. 7, two pieces of tissue 80 and 82 are to be joined using a suture 84. A distal anchor 86 is located on the end of the suture 84. The suture is then inserted through the tissues 82 and 80 so that a free end 88 of the suture 84 protrudes at the proximal end. A fastener 90 having an opening 92 therein is slid over the wire 84 and pulled down tight as shown in FIG. 7C to close the gap 94 between the tissues 80 and 82.

The fastener 90 is made of a heat bondable plastic material. (The suture can also be made of heat bondable plastic material which is bonded to secure the connection.) The fastener 90 is then bonded at an area 96 to the protruding free end 88 of the suture 84. In FIG. 7C, it can be seen that the fastener 90 is bonded to the suture 84 without significant deformation of the suture. Alternatively, the fastener 90 can be bonded along the length of the opening 92 to the suture 84. The protruding end of the suture 84 is then cut off. Applicant has found through testing that while a simple mechanical connection such as a knot or a crimped connector is not strong enough to hold in some circumstances, the bonded connection illustrated in FIG. 7 overcomes this difficulty and will hold.

FIG. 8 illustrates a few of the many fasteners which can be used in accordance with the present invention. FIG. 8A shows a simple square fastener 100 having a suture receiving opening 102 therein. The fastener 104 is round and has an opening 106 therein. The fastener 108 shown in FIG. 8C includes a plurality of barbs 110 for better gripping in the tissue against which it engages. The fastener 112 shown in FIG. 8 is umbrella-like in shape, having an outer rib 114 and a plurality of radially extending ribs 116.

The fastener 118 shown in FIG. 8E is filamentous, having a plurality of protruding filaments 120. The fastener 122 shown in FIG. 8F is a T-snap. The fastener 124 shown in FIG. 8G is curved or cupped about the opening 126 so that its ends 128 and 130 will flatten as pressure is applied upon drawing tight the suture. The fastener 132 shown in FIGS. 8H and 8I is reinforced with transverse ribs 134 and longitudinal ribs 136 for better strength. The ribs 134 and 136 protrude axially from the main body 138 of the fastener. Finally, any anchor or fastener can be specially made, that is, custom molded at the time of the surgery or preoperatively to conform exactly to the tissue against which it will be abutting.

FIG. 9 illustrates the use of an expandable distal suture anchor for bonded suture fastenings in accordance with the present invention. In particular, FIG. 9 illustrates the use of a bonded assembly to secure a tendon 140 to bone 142. To make the assembly, initially, a cannula or sleeve 144 is inserted through the tendon to the bone. A gouge 146 is then used to gouge out an opening 148 in the soft cancellous tissue under the cortical bone. An expandable anchor 150, confined in a sleeve 152 and having a suture 154 extending proximally from the sleeve 152, is inserted through the canula 144 into the opening 148 in the bone. The sleeve 152 is then withdrawn, allowing the anchor 150 to expand within the opening 148, blocking removal of the suture.

Figure 9D:
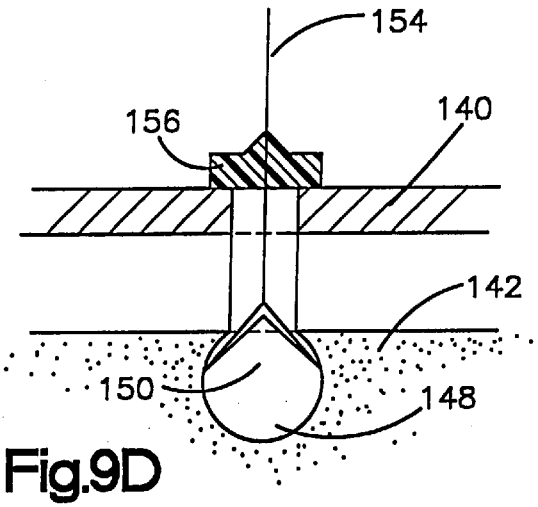

A fastener 156 made of or including a bondable plastic material is then slid distally over the suture 154 into engagement with the tendon 140, and then further, pushing the tendon 140 into engagement with the bone 142. The anchor 156 is then bonded to the suture 154, providing a connection which is stronger than that of any tied knot. In FIG. 9D, it can be seen that the fastener 156 is bonded to the suture 154 without significant deformation of the suture. In a similar manner, an expandable anchor as illustrated herein can be used with a bonded fastening in any application in which the anchor must be placed in a blind location. This method can work also especially well with a barbed or umbrella-like anchor as illustrated in FIG. 8C or 8D.

FIG. 10 illustrates the use of bonded fastenings in accordance with the present invention in conjunction with a curved opening in tissue parts to be joined. Illustrated in FIG. 10 are two portions 172 and 174 of a fractured bone with their ends abutting at a joint 176. It is possible to secure together the bone ends with a suture which extends axially through the fractured ends of the bone, while accessing the joint only from one side of the bone. A curved opening 178 is drilled through the first bone part 172 and the second bone part 174, beginning at the proximal end of the first bone part 172, extending through the joint 176, and exiting at the proximal face of the second bone part 174. A suture 180 is then passed through the opening 178. A first fastener 182 made of or including a bondable plastic material is then bonded onto the protruding end of the suture 180. The suture is then pulled tight, and a second fastener 184 also made of or including a bondable material is pulled down tight against the proximal face of the second bone part 174 and bonded by heating in location to the suture 180. In FIG. 10, it can be seen that the fasteners 182 and 184 are bonded to the suture 180 without significant deformation of the suture.

FIG. 11 illustrates the use of a bonded fastening in accordance with a feature of the present invention in conjunction with a rivet type fastening. To secure together two adjoining masses 186 and 188, a sleeve 190 is inserted through an opening in the tissues until the distal end 192 of the sleeve projects behind the tissue 186. A mandrel 194 in the sleeve 190 has a headed portion 196 at its distal end 192. The mandrel 194 is then pulled outwardly, while the sleeve 190 is held in place, spreading the distal end 192 of the sleeve to lock the sleeve in place behind tissue 186. The protruding end of the mandrel 194 is then cut off flush with and bonded by heating as at 198 to the head end 200 of the sleeve. This type of bonded connection can be used in various applications where the surgeon is connecting two tissue masses with access only from one side thereof.

The present invention also is embodied in a method of making an assembly for use in surgical applications in humans. The method comprises the steps of providing a first component which comprises a heat bondable plastic material; providing a second component; and bonding the first and second components to each other by the application of heat to the heat bondable material to make the heat bondable material bond to the other component. In the method, the second component may be a surgical prosthesis or implant, or it may be a bone plate or bone screw. The heat bondable plastic material used in the method may be a polymer, a composite, or a biodegradable material.

The present invention also is embodied in a method of fastening a suture or K-wire to hold together adjoining tissue masses in a human surgical application. The method comprises the steps of inserting the suture into the desired location in the tissue masses, placing in position on the suture a suture fastener, and bonding the suture to the fastener by applying heat to one or both of the fastener and the suture to bond the fastener to the suture. Further, the fastener may be mechanically crimped first and then heat bonded to provide the benefits of both types of fastenings.

The present invention is also embodied in a kit of components for forming an assembly by heat bonding for use in surgical applications in humans and incorporating at least one heat bondable material. The kit comprises a first component and a second component comprising a heat bondable material, with the first and second components bondable to each other upon the application of heat to the second component to make the heat bondable material of the second component bond to the first component. The kit may further include heat generating means for generating heat to bond said first component to said second component. The components and the heat generating means are as described above with respect to the assemblies.

Method and apparatus for Suturing Body Tissue

An apparatus 220 for use in suturing human body tissue (FIG. 12) includes a retainer or crimp 222 and a suture 224.

The suture 224 extends through a layer 226 of skin into body tissue 228 disposed beneath the skin. Although the suture 224 as been illustrated in FIG. 12 in association with soft body tissue 226 and 228, it is contemplated that the suture 224 could be used in association with relatively hard body tissue, such as bone. The suture 224 may be placed in many different locations in the human body for many different purposes. For example the suture 224 may be used with a suture anchor in the manner disclosed in U.S. Pat. No. 5,403,348 issued Apr. 4, 1995 and entitled Suture Anchor.

The retainer 222 is formed of a plastic material. The suture 224 is also formed of a plastic material. The retainer 222 is bonded to the suture 224 without significant deformation of the suture. This enables the retainer 222 to securely hold the suture relative to the body tissue 226 and 228 without impairing the strength of the suture. Although the retainer 222 has been shown in FIG. 12 as being connected with opposite end portions of a single suture 224, the retainer could be connected with end portions of two separate sutures.

In the illustrated embodiment of the invention, the retainer 222 has a generally cylindrical configuration (FIGS. 12 and 13). The retainer 222 has a pair of linear cylindrical passages 232 and 234 through which the suture 224 extends. Thus, a portion 238 of the suture 224 extends through the passage or opening 232. A portion 240 of the suture extends through the passage or opening 234 (FIG. 12).

In the suture arrangement illustrated in FIG. 12, a connector portion 242 of the suture 224 interconnects the two portions 238 and 240. If desired, the connector portion 242 of the suture 224 could extend through a suture anchor. It is contemplated that the connector portion 242 of the suture 224 could extend around ligaments or other human body tissue. It is contemplated that the retainer 222 could be used to interconnect sutures in a series of sutures.

After the two portions 238 and 240 of the suture 224 have been inserted into the passages or opening 232 and 234 in the retainer 222, the retainer and suture are interconnected to hold the suture against movement relative to the body tissue. To interconnect the retainer and the portion 238 of the suture 224, the plastic material of the retainer 222 is heated to a temperature in a transition temperature range of the plastic material of the retainer 222. The plastic material of the suture 224 is maintained at a temperature below the transition temperature range of the plastic material forming the suture.

Thus, in the specific embodiment of the invention illustrated in FIGS. 12–15, the plastic material of the suture 224 has a transition temperature range which is above 190° Celsius. The specific retainer 222 illustrated in FIGS. 12–15 has a transition temperature range which is below 190° Celsius. However, it should be understood that at least a portion of or even the entire transition temperature range for the suture 224 could be coextensive with the transition temperature range for the retainer 222. In fact, the transition temperature range of the suture could extend below the transition temperature range of the retainer. However, it is believed that it will be advantageous to have a higher transition temperature range for the suture than for the retainer.

Once the plastic material of the retainer 222 has been heated to a temperature in the transition temperature range for the plastic material of the retainer, the plastic material of the retainer flows around the plastic material of the suture 224. This occurs while the plastic material of the suture 224 is maintained at a temperature below the transition temperature range of the plastic material of the suture. Thus, the portion of the plastic material of the retainer 222 forming the passage 232 (FIG. 14) is heated to a temperature in its transition temperature range. The plastic material of the retainer 222 then flows inwardly around the portion 238 of the suture 224 to eliminate the passage 232 (FIG. 15).

As this occurs, the portion 238 of the suture 224 maintains its original configuration and is not significantly deformed. Thus, an outer side surface 242 of the suture 224 has the same cylindrical configuration along the length of the suture both in the areas where the outer side surface of the suture is exposed to the heated material of the retainer 224 and in the areas where the suture is not exposed to the heated material of the retainer 222. By maintaining the configuration of the portion 238 of the suture exposed to the heated material of the retainer 222 constant, the suture 224 is not weakened in the areas where it is exposed to the heated material of the retainer.

After the material of the retainer 222 has been heated and flows around the portions 238 and 240 of the suture 224, in the manner illustrated schematically for the portion 238 of the suture in FIG. 15, the heated plastic material of the retainer is cooled to a temperature below the transition temperature range of the plastic material of the retainer. As the plastic material of the retainer is cooled to a temperature below its transition temperature range, the plastic material of the retainer bonds to the suture 224. Thus, the plastic material of the retainer 222 bonds to the portion 238 of the suture 224 and bonds to the portion 240 of the suture.

As the plastic material of the retainer 222 is cooled and bonds to the outer side surface 242 of the suture 224, a secure interconnection occurs between the material of the retainer 222 and the material of the suture 224 at the portions 238 and 240 of the suture. The interconnection between the material of the retainer 222 and the material of the portion 238 and 240 of the suture is the result of both molecular attraction (adhesion) of the material of the retainer 222 to the material of the suture 224 and due to a mechanical interconnection between the material of the retainer 222 and the material of the suture 224. Thus, as the material of the retainer 222 cools, it mechanically grips the suture 224 so that the suture is held against movement relative to the retainer by interfacial forces between the material of the retainer and the material of the suture. Thus, there is a fusing of the material of the retainer 222 to the material of the suture 224 along the portions 238 and 240 of the suture.

The suture 224 is formed of a plastic material which may be a biopolymer. In one specific embodiment of the invention, the suture is formed of polyglycolide (P-G) ($C_4H_4O_4$) which is commercially available under the trademark Dexon. Polyglycolide is a crystalline material (40–55% crystallinity) that melts at about 225° Celsius. Although the suture 224 is a monofilament suture having a continuous cylindrical outer side surface 242, it is contemplated that this suture could be formed in a different manner. For example, the suture could be a braided suture.

It is also contemplated that the suture 224 may be formed of a high glycolide-based copolymer, specifically a 10/90 P-LL/G (10% poly l-lactide and 90% glycolide) which is commercially available under the trademark "Vicryl". "Vicryl" is a crystalline material that melts at about 205° Celsius. "Vicryl" can be used for either a monofilament or braided suture.

The retainer 222 is also a plastic material which may be a biopolymer. In one specific embodiment of the invention, the retainer 222 is formed of poly dl lactide (P-DLL) ($C_6H_8O_4$) and is amorphous and has a processing temperature of approximately 120° Celsius. The transition temperature range of poly dl lactide will vary depending upon the specific characteristics of the material. However, the retainer 222 of FIGS. 12–15 had a transition temperature range of from about 75° Celsius to about 120° Celsius.

In another specific embodiment of the invention, the retainer 222 is formed of poly dl lactide (P-DLL) ($C_6H_8O_4$) and poly l lactide (P-LL) ($C_6H_8O_4$) copolymer and is a material having a melt temperature of approximately 165° Celsius. The transition temperature range of the poly dl lactide and poly l lactide copolymer will vary depending upon the specific characteristics of the copolymer and is from about 75° Celsius to about 180° Celsius. In still another specific embodiment of the invention, the retainer 222 is formed of poly l lactide (P-LL) and has a melt temperature of approximately 145°–185° Celsius. A transition temperature range of poly l lactide is from about 70° Celsius to about 185° Celsius.

It is contemplated that the retainer 222 may be formed of many different types of plastic materials. However, it is believed that biopolymers may be preferred. It is contemplated that polymers of lactic acid, lactides l-lactides, and isomers of lactic acids and/or lactides may be preferred. Of course, the suture 224 can also be formed of many different types of plastic materials.

Although it is presently preferred to form the suture 224 and retainer 222 of different materials, the suture and retainer could be formed of the same material if desired. By forming the suture 224 of a material having a transition temperature range which is at least partially above the transition temperature range of the retainer 222, bonding of the retainer to the suture without significant deformation of the suture is facilitated.

In the embodiment of the retainer 222 illustrated in FIGS. 12 and 13, the plastic material of the retainer 222 is heated to a temperature in its transition temperature range by applying heat to a portion of the retainer disposed between the two passages 232 and 234. This results in a central portion of the plastic material forming the retainer 222 being heated into its transition temperature range while the outer circumference of the cylindrical retainer 222 is maintained at a temperature below the transition temperature range of the plastic material of the retainer.

In the specific embodiment of the retainer 222 illustrated in FIGS. 12 and 13, a generally conical recess 250 is formed in the central portion of the retainer 222. The recess 250 (FIG. 13) is spaced equal distances from the passages 232 and 234 and has a central axis which is parallel to the central axes of the passages 232 and 234. The central axis of the recess 250 is coincident with a central axis of the cylindrical retainer 222. In this specific embodiment of the invention, a heater element 254 having a conical end portion 256 is used to heat the retainer 222. Of course, other devices, such as a laser, could be used to heat the retainer 222.

After the portions 238 and 240 of the suture 224 have been inserted into the openings or passages 232 and 234 and the suture and retainer moved to the desired positions relative to the body tissue 226 and 228, the heater element 254 is inserted into the recess 250. Heat is conducted from the heater element 224 to the plastic material in the central portion of the retainer 222. The plastic material in the central portion of the retainer 222 is heated into its transition temperature range. As this occurs, the plastic material in the central portion of the retainer 222 changes from a solid condition in which it has a fixed form to a viscous condition. The plastic material adjacent to the cylindrical outer side surface of the retainer is not heated into the transition temperature range and maintains its original configuration.

When the plastic material in the central portion of the retainer 222 has been heated into the transition temperature range and has a viscous condition, the material readily flows and molds itself around the outer side surface 242 (FIG. 15) of the suture 224. As this occurs, the configuration of the suture 224 remains unaltered and there is no significant deformation of the suture 224. The heating element 254 is then removed from the recess 250 and the plastic material of the retainer 222 is cooled to a temperature below the transition temperature of the material. As the plastic material of the retainer 222 is cooled to a temperature below its transition temperature, the plastic material bonds to the suture 224 to provide a solid interconnection between the retainer and the suture.

In the embodiment of the invention illustrated in FIGS. 12–15, the suture 224 is a monofilament suture. In the embodiment of the invention illustrated in FIG. 16, the suture is a braided suture. Since the embodiment of the invention illustrated in FIG. 16 is generally similar to the embodiment of the invention illustrated in FIGS. 12–15, similar numerals will be utilized to designate similar components, the suffix letter (a) being associated with the embodiment of the invention illustrated in FIG. 16 to avoid confusion.

A retainer 222a formed of a plastic material is bonded to a suture 224a by heating the plastic material of the retainer 222a into its transition temperature range. After the plastic material of the retainer 222a has flowed around the suture 224a while the plastic material of the suture is at a temperature below the transition temperature range of the plastic material of the suture, the plastic material of the retainer is cooled to a temperature below the transition temperature range of the plastic material of the retainer. As the plastic material of the retainer 222a is cooled, a secure bond is obtained between the plastic material of the retainer 222a and the suture 224a. This secure bond is obtained without significant deformation of the suture 224a.

Figure 16:
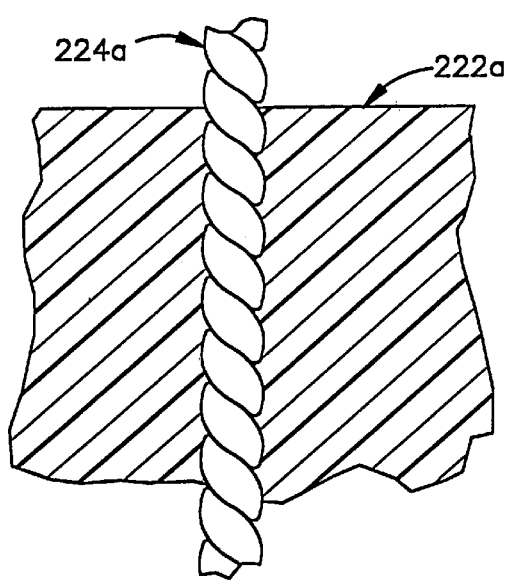
FIG. 16 is a fragmentary sectional view generally similar to FIG. 15, illustrating the manner in which the retainer is bonded to a braided suture.

In accordance with a feature of the embodiment of the invention illustrated in FIG. 16, the suture 224a is a braided suture. Thus, the suture 224a is formed by plurality of monofilament strands which are intertwined to form the braided suture 224a. When the plastic material of the retainer 222a is heated to a temperature above its transition temperature, the plastic material of the retainer 222a flows between and around the strands of the braided suture 224a. Upon cooling of the plastic material of the retainer 222a to a temperature below its transition temperature, a secure bond is obtained between the material of the retainer 222a and the strands of the braided suture 224a.

Figure 17:
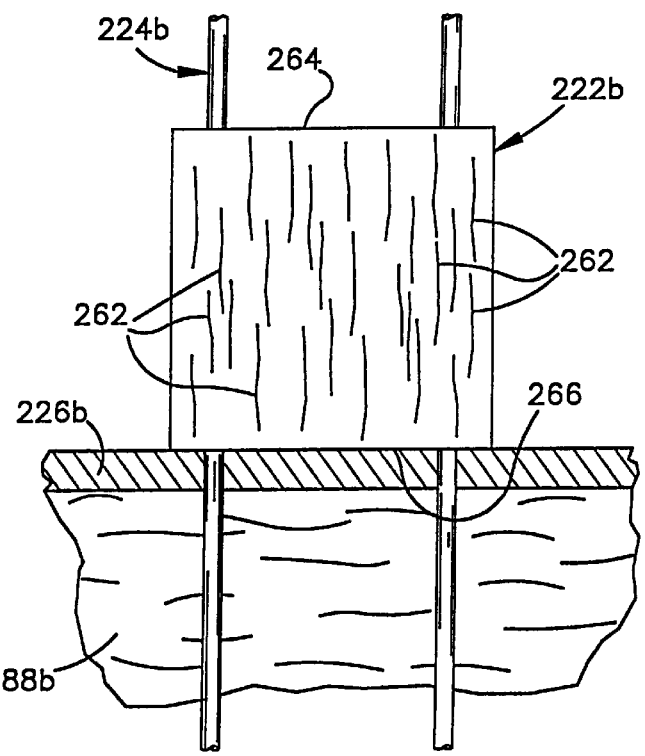
FIG. 17 is a schematic illustration, generally similar to FIG. 12, schematically illustrating the orientation of polymer chains relative to the retainer.

In the embodiment of the invention illustrated in FIG. 17, the polymer chains of the plastic material forming the retainer are oriented relative to the suture. The orientation of the polymer chains of the retainer are such that the bonding which is obtained between the suture and the retainer includes a mechanical interconnection due to contracting of the polymer chains as the plastic material of the retainer is heated. Since the embodiment of the invention illustrated in FIG. 17 is generally similar to the embodiment of the invention illustrated in FIGS. 12–15, similar numerals will be utilized to designate similar components, the suffix letter "b" being associated with the numerals of FIG. 17 in order to avoid confusion.

The retainer 222b has a generally cylindrical configuration. The suture 224b has portions which extend through the retainer 222b. Portions of the suture 224b are disposed in passages (not shown) corresponding to the passages 232 and 234 of FIG. 12. The retainer 222b and suture 224b are formed of the same plastic materials as the retainer 222 and suture 224 of FIGS. 12–15.

In accordance with a feature of the embodiment of the invention illustrated in FIG. 17, the retainer 222b has polymer chains, illustrated schematically by lines 262, which are disposed in a predetermined orientation relative to the retainer 222b. In the illustrated embodiment of the invention, the polymer chains 262 are orientated with their longitudinal axes extending parallel to the central axis of the cylindrical retainer 222b and parallel to the longitudinal axes of the portions of the suture 224b disposed within passages in the retainer.

Upon heating of the central portion of the retainer 222b, the polymer chains 262 of the plastic material in the central portion of the retainer 222b contract in an axial direction. Thus, the distance between circular end surfaces 264 and 266 of the retainer 222b decreases to a greater extent and the outside diameter of the retainer 222b. This results in a mechanical gripping of the portions of the suture 224b disposed within the retainer 222b by the plastic material of the retainer.

In the embodiments of the invention illustrated in FIGS. 12–17, portions of the suture are disposed in cylindrical passages which extend through the retainer and have central axes which are parallel to a central axis of the retainer. In the embodiment of the invention illustrated in FIG. 18, portions of the suture extend through retainer passages which are skewed relative to the central axis of the retainer. Since the embodiment of the invention illustrated in FIG. 18 is generally similar to the embodiments of the invention illustrated in FIGS. 12–17, similar numerals will be utilized to designate similar components, the suffix letter "c" being associated with the numerals of FIG. 18 to avoid confusion.

Figure 18:
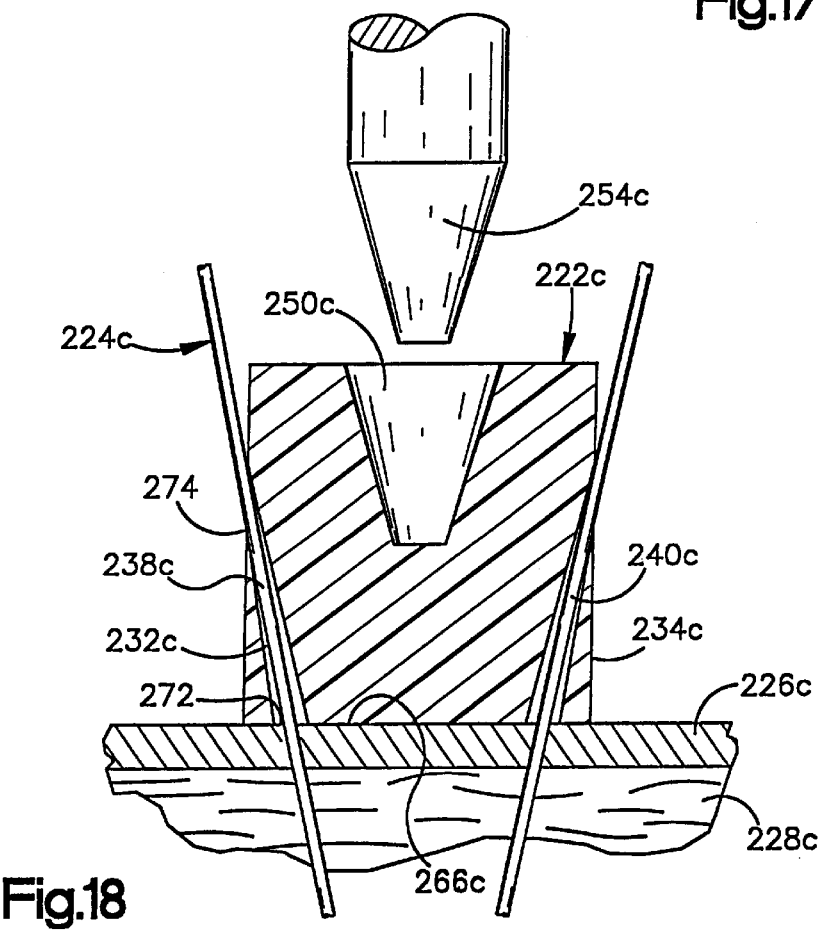
FIG. 18 is a fragmentary sectional view, generally similar to FIG. 12, illustrating a second embodiment of the retainer.

In the embodiment of the invention illustrated in FIG. 18, a cylindrical retainer 222c is formed of a plastic material. A pair of passages 232c and 234c are formed in the retainer 222c. A suture 224c, formed of a plastic material, has portions 238c and 240c which are received in the passages or openings 232c and 234c. A central recess 250c is formed in the retainer 222c to receive a heater element 254c when the plastic material of the retainer 222c is to be heated. The retainer 222c and suture 224c are formed of the same plastic materials as the retainer 222 and suture 224 of FIGS. 12–15.

In accordance with a feature of the embodiment of the invention illustrated in FIG. 18, the passages 232c and 234c have central axes which are skewed in an acute angle to the central axis of the retainer 222c. Thus, the suture 224c is inserted into the passage 232c through a circular opening 272 in a circular end surface 266c of the retainer 222c. The passage 232c has axially tapering side surface which forms a portion of a cone. The axially tapering configuration of the side surface of the passage 232c enables the side surface of the passage to securely grip the suture 224c at a location where an oval opening 274 is formed in the cylindrical outer side surface of the retainer 222c. The longitudinal central axis of the passage 232c is skewed at an acute angle relative to the central axis of the cylindrical retainer 222c.

The portion 240c of the suture 224c is inserted into the passage 234c. The passage 234c has the same tapered configuration as the passage 232c. The longitudinal central axis of the passage 234c is skewed at an acute angle to the central axis of the cylindrical retainer 222c. The longitudinal central axis of the passage 234c is also skewed at an acute angle to the central axis of the passage 232c.

During use of the apparatus illustrated in FIG. 18, the suture 224c is placed in a desired position relative to body tissue 226c and 228c. The portions 238c and 240c are then inserted through the passages 232c and 234c in the retainer 222c. The suture 224c the then tightened to position the retainer 222c relative to the body tissue 226c and 228c.

Once this has been done, the material of the retainer 222c is heated by inserting a heater element 254c into the recess 250c in the central portion of the retainer 222c. In this specific embodiment of the retainer 222c illustrated in FIG. 18, the polymer chains of the plastic material forming the retainer 222c are oriented with their longitudinal axes extending parallel to the longitudinal central axis of the retainer 222c, in the same manner as illustrated schematically by the lines 262 for the retainer 222b in FIG. 17. Therefore, upon heating of the retainer 222c, the polymer chains contract to grip the portions 232c and 234c under the influence of forces extending transversely to the longitudinal central axes of the portion 238c and 240c of the suture 224c.

As the material in the central portion of the retainer 222c is heated into its transition temperature range, the material of the retainer flows around the portions 238c and 240c of the suture 224c disposed in the passages 232c and 234c. The temperature of the material forming the retainer 222c is maintained at a temperature which is below the transition temperature for the plastic material of the suture 224c. Therefore, the plastic material of the retainer 222c flows around the plastic material of the suture 224c without significant deformation of the suture.

A secure bonding of the plastic material of the retainer 222c to the plastic material of the suture 224c is obtained by cooling the material of the retainer to a temperature below its transition temperature. This secure bonding is obtained without significant deformation of the suture 224c so that the suture maintains its strength and is capable of holding the body tissue 226c and 228c in a desired manner.

From the foregoing, it is apparent that the apparatus and methods of the embodiments of the invention illustrated in FIGS. 12–18 may be used in suturing body is tissue. A portion 238 of a suture 224 is inserted into an opening in a retainer 222 formed of a plastic material. At least a portion of the retainer 222 is heated to a temperature in a transition temperature range of the plastic material forming the retainer. The suture 224 is maintained at a temperature below the transition temperature range of a plastic material forming the suture while the retainer 222 is heated. The plastic material of the retainer 222 flows around the plastic material of the suture 224. A bonding of the plastic material of the retainer 222 to the plastic material of the suture 224 is effected by cooling the plastic material of the retainer to a temperature below its transition temperature range. The foregoing steps are performed without significant deformation of the plastic material of the suture 224. It should be understood that the plastic materials of the sutures and retainers of the embodiments of the invention illustrated in FIGS. 16–18 are interconnected in the same manner as the embodiment of FIGS. 12–15.

From the above description of the invention, those skilled in the art will perceive improvements, changes and modifications. Such improvements, changes and modifications within the skill of the art are intended to be covered by the appended claims.

The following is claimed:

1. A method comprising the steps of moving an anchor connected with a suture into engagement with a first segment of body tissue, said step of moving an anchor connected with a suture into engagement with a first segment of body tissue includes embedding the anchor in the first segment of body tissue with the suture connected with the anchor and extending from the first segment of body tissue and expanding the anchor while the anchor is disposed in the body tissue, moving at least the suture through a second segment of body tissue, thereafter, moving a retainer along the suture toward the second segment of body tissue, pressing the first and second segments of body tissue together, said step of pressing the first and second segments of the body tissue together includes tensioning the suture, transmitting force from the suture through the anchor to the first segment of body tissue, transmitting force from retainer to the second segment of body tissue while maintaining the portion of the suture between the anchor and the retainer straight under the influence of tension in the suture, gripping the suture with the retainer by plastically deforming the retainer while continuing to press the first and second segments of the body tissue together, thereafter, transmitting force between the suture anchor and retainer to continue to press the first and second segments of body tissues together while maintaining the portion of the suture between the anchor and the retainer straight under the influence of tension in the suture.

2. A method as set forth in claim 1 wherein said step of embedding the anchor in the first segment of the body tissue includes changing the orientation of at least a portion of the anchor relative to the body tissue.

3. A method as set forth in claim 1 wherein said step of embedding the anchor in the body tissue includes moving the anchor into the body tissue and increasing the extent of the anchor in a direction transverse to a longitudinal axis of the suture while the anchor is in the body tissue.

4. A method as set forth in claim 1 wherein said step of moving at least the suture through a second segment of body tissue includes moving the anchor and a portion of the suture through the second segment of body tissue.

5. A method as set forth in claim 1 wherein said step of gripping the suture with the retainer includes connecting the retainer with the suture without significant deformation of the suture.

6. A method as set forth in claim 1 wherein said step of gripping the suture with the retainer includes bonding the retainer to the suture.

7. A method as set forth in claim 1 wherein said step of gripping the suture with the retainer includes heating the retainer and bonding the material of the retainer to the suture.

8. A method as set forth in claim 1 wherein a first end portion of the suture is connected with the anchor, said step of gripping the suture with the retainer includes inserting a second end portion of the suture through an opening in the retainer and moving at least a portion of a side surface of the opening in the retainer into engagement with an outer side surface of the suture.

9. A method as set forth in claim 1 wherein said step of plastically deforming the retainer includes heating at least a portion of material forming the retainer into a transition temperature range of the material of the retainer.

10. A method as set forth in claim 1 wherein the retainer has polymer chains oriented in a direction extending along a longitudinal axis of a portion of the suture, the polymer chains being contracted to cause material of the retainer to grip the suture.

11. A method comprising the steps of moving an anchor into a bone through an opening in a surface on the bone with a suture connected to the anchor, moving a suture retainer along the suture toward the bone, tensioning the suture, retaining the anchor against movement relative to the bone under the influence of force transmitted between the anchor and the bone while tensioning the suture, and securing the suture retainer against movement relative to the suture while tensioning the suture and retaining the anchor against movement relative to the bone under the influence of force transmitted to the anchor through the suture by transmitting force between the anchor and the bone, said step of securing the suture retainer against movement relative to the suture includes gripping the suture with the suture retainer by deforming the suture retainer while continuing to tension the suture.

12. A method as set forth in claim 11 further including the step of pressing body tissue against the surface on the bone under the influence of force transmitted to the body tissue from the suture retainer.

13. A method as set forth in claim 11 wherein said step of moving the anchor through an opening in a surface on the bone is performed with the anchor in a first orientation relative to the bone, said step of retaining the anchor against movement relative to the bone includes changing the orientation of the anchor from the first orientation to a second orientation relative to the bone.

14. A method as set forth in claim 11 wherein said step of retaining the anchor against movement relative to the bone includes transmitting force from the anchor to soft cancellous bone tissue.

15. A method comprising the steps of moving an anchor into a bone through an opening in a surface on the bone with a suture connected to the anchor, moving a suture retainer along the suture toward the bone, tensioning the suture, retaining the anchor against movement relative to the bone under the influence of force transmitted between the anchor and the bone while tensioning the suture, said step of retaining the anchor against movement relative to the bone includes expanding the anchor after performing said step of moving the anchor through an opening in a surface on the bone, and securing the suture retainer against movement relative to the suture while tensioning the suture and retaining the anchor against movement relative to the bone under the influence of force transmitted to the anchor through the suture by transmitting force between the anchor and the bone.

16. A method as set forth in claim 15 further including the step of pressing body tissue against the surface on the bone under the influence of force transmitted to the body tissue from the suture retainer.

17. A method as set forth in claim 15 wherein said step of securing the suture retainer against movement relative to the suture includes gripping the suture with the suture retainer by deforming the suture retainer while continuing to tension the suture.

18. A method as set forth in claim 15 wherein said step of moving the anchor through an opening in a surface on the bone is performed with the anchor in a first orientation relative to the bone, said step of retaining the anchor against movement relative to the bone includes changing the orientation of the anchor from the first orientation to a second orientation relative to the bone.

19. A method as set forth in claim 15 wherein said step of retaining the anchor against movement relative to the bone includes transmitting force from the anchor to soft cancellous bone tissue.

20. A method as set forth in claim 15 wherein said step of securing the suture retainer against movement relative to the suture includes heating at least a portion of material forming the suture retainer into a transition temperature range of the material of the suture retainer.

21. A method as set forth in claim 15 wherein the suture retainer has polymer chains oriented in direction extending along a longitudinal axis of a portion of the suture, the polymer chains being contracted to cause material of the suture retainer to grip the suture.

22. A method of connecting body tissue with bone, said method comprising the steps of moving an anchor through the body tissue into the bone with a suture connected to the anchor, moving a suture retainer along the suture toward the body tissue and bone, tensioning the suture, retaining the anchor against movement relative to the bone under the influence of force transmitted between the anchor and bone while tensioning the suture, said step of retaining the anchor against movement relative to the bone includes embedding the anchor in the bone with the suture connected to the anchor and extending through the body tissue, said step of embedding the anchor in the bone includes expanding the anchor while the anchor is in the bone, transmitting force from the suture retainer to the body tissue to press the body tissue against the bone while performing said steps of tensioning the suture and retaining the anchor against movement relative to the bone, and securing the suture retainer against movement relative to the suture while tensioning the suture and retaining the anchor against movement relative to the bone.

23. A method as set forth in claim 22 wherein said step of securing the suture retainer against movement relative to the suture includes heating at least a portion of material forming the suture retainer into a transition temperature range of the material of the suture retainer.

24. A method as set forth in claim 22 wherein the suture retainer has polymer chains oriented in a direction extending along a longitudinal axis of a portion of the suture, the polymer chains being contracted to cause material of the suture retainer to grip the suture.

25. A method as set forth in claim 22 wherein said step of moving the anchor through the body tissue into the bone includes moving the anchor into the bone along a first path of movement, said step of moving the suture retainer along the suture toward the body tissue and bone includes moving the suture retainer along the first path of movement.

26. A method as set forth in claim 22 wherein said step of embedding the anchor in the bone includes changing the orientation of at least a portion of the anchor relative to the bone.

27. A method as set forth in claim 22 wherein said step of embedding the anchor in the bone includes moving the anchor into the bone and increasing the extent of the anchor in a direction transverse to a longitudinal central axis of the suture while the anchor is in the bone.

28. A method as set forth in claim 22 wherein said step of securing the suture retainer against movement relative to the suture includes connecting the suture retainer with the suture without significant deformation of the suture.

29. A method as set forth in claim 22 wherein said step of securing the suture retainer against movement relative to the suture includes bonding the suture retainer to the suture.

30. A method as set forth in claim 22 wherein said step of securing the suture retainer against movement relative to the suture includes heating the suture retainer and bonding material of the suture retainer to the suture.

31. A method as set forth in claim 22 wherein said step of securing the suture retainer against movement relative to the suture includes gripping the suture with the suture retainer by deforming the suture retainer while continuing to tension the suture.

32. A method comprising the steps of connecting a suture which is formed separately from an anchor with the anchor, moving the anchor connected with the suture into engagement with a first segment of body tissue, moving at least the suture through a second segment of body tissue, thereafter, moving a retainer along the suture toward the second segment of body tissue, moving at least one of the first and second segments of body tissue relative to the other segment of body tissue while performing said step of moving a retainer along the suture toward the second segment of body tissue, pressing the first and second segments of body tissue together, said step of pressing the first and second segments of the body tissue together includes tensioning the suture, transmitting force from the suture through the anchor to the first segment of body tissue, transmitting force from a retainer to the second segment of body tissue while maintaining tension in the suture, gripping the suture with the retainer by plastically deforming the retainer while continuing to press the first and second segments of the body tissue together and while maintaining tension in the suture, and, thereafter, transmitting force between the suture anchor and retainer to continue to press the first and second segments of body tissue together while maintaining tension in the suture.

33. A method as set forth in claim 32 wherein said step of moving an anchor into the first segment of body tissue includes moving the anchor into the body tissue in a first direction relative to the body tissue, said step of moving the retainer along the suture toward the second segment of body tissue includes sliding the retainer along the suture in the first direction relative to the body tissue.

34. A method as set forth in claim 32 wherein said step of moving an anchor connected with a suture into a first segment of body tissue includes embedding the anchor in the first segment of body tissue with the suture connected with the anchor and extending from the first segment of body tissue.

35. A method as set forth in claim 32 wherein said step of moving the anchor connected with the suture into engagement with a first segment of body tissue includes expanding the anchor while the anchor is disposed in the body tissue.

36. A method as set forth in claim 32 wherein said step of moving the anchor connected with the suture into engagement with a first segment of body tissue includes changing the orientation of at least a portion of the anchor relative to the body tissue while the anchor is in engagement with the body tissue.

37. A method as set forth in claim 32 wherein said step of moving the anchor connected with the suture into engagement with a first segment of body tissue includes moving the anchor into the body tissue and increasing the extent of the anchor in a direction transverse to a longitudinal axis of the suture while the anchor is in the body tissue.

38. A method as set forth in claim 32 wherein said step of moving at least the suture through a second segment of body tissue includes moving the anchor and a portion of the suture through the second segment of body tissue.

39. A method as set forth in claim 32 wherein said step of gripping the suture with the retainer includes connecting the retainer with the suture without significant deformation of the suture.

40. A method as set forth in claim 32 wherein said step of gripping the suture with the retainer includes bonding the retainer to the suture.

41. A method as set forth in claim 32 wherein said step of gripping the suture with the retainer includes heating the retainer and bonding the material of the retainer to the suture.

42. A method as set forth in claim 32 wherein a first end portion of the suture is connected with the anchor, said step of gripping the suture with the retainer includes inserting a second end portion of the suture through an opening in the retainer and moving at least a portion of a side surface of the opening in the retainer into engagement with an outer side surface of the suture.

43. A method as set forth in claim 32 wherein said step of plastically deforming the retainer includes heating at least a portion of material forming the retainer into a transition temperature range of the material of the retainer.

44. A method as set forth in claim 32 wherein the retainer has polymer chains oriented in a direction extending along a longitudinal axis of a portion of the suture, the polymer chains being contracted to cause material of the retainer to grip the suture.

45. A method of connecting body tissue with bone, said method comprising the steps of connecting a suture which is formed separately from an anchor with the anchor, moving the anchor into the bone with the suture connected to the anchor, moving a suture retainer along the suture toward the body tissue and bone, tensioning the suture while moving the suture retainer along the suture toward the body tissue and bone, retaining the anchor against movement relative to the bone under the influence of force transmitted between the anchor and bone while tensioning the suture, transmitting force from the suture retainer to the body tissue to press the body tissue against the bone while performing said steps of tensioning the suture and retaining the anchor against movement relative to the bone, and securing the suture retainer against movement relative to the suture while tensioning the suture and retaining the anchor against movement relative to the bone.

46. A method as set forth in claim 45 wherein said step of moving the anchor into the bone includes moving the anchor into the bone along a first path of movement, said step of moving the suture retainer along the suture toward the body tissue and bone includes moving the suture retainer along the first path of movement.

47. A method as set forth in claim 45 wherein said step of retaining the anchor against movement relative to the bone includes embedding the anchor in the bone with the suture connected to the anchor and extending through the body tissue.

48. A method as set forth in claim 45 wherein said step of retaining the anchor against movement relative to the bone includes expanding the anchor while the anchor is in the bone.

49. A method as set forth in claim 45 wherein said step of retaining the anchor against movement relative to the bone includes changing the orientation of at least a portion of the anchor relative to the bone.

50. A method as set forth in claim 45 wherein said step of retaining the anchor against movement relative to the bone includes moving the anchor into the bone and increasing the extent of the anchor in a direction transverse to a longitudinal central axis of the suture while the anchor is in the bone.

51. A method as set forth in claim 45 wherein said step of securing the suture retainer against movement relative to the suture includes connecting the suture retainer with the suture without significant deformation of the suture while continuing to tension the suture.

52. A method as set forth in claim 45 wherein said step of securing the suture retainer against movement relative to the suture includes bonding the suture retainer to the suture while continuing to tension the suture.

53. A method as set forth in claim 45 wherein said step of securing the suture retainer against movement relative to the suture includes heating the suture retainer and bonding material of the suture retainer to the suture while continuing to tension the suture.

54. A method as set forth in claim 45 wherein said step of securing the suture retainer against movement relative to the suture includes gripping the suture with the suture retainer by deforming the suture retainer while continuing to tension the suture.

55. A method as set forth in claim 45 wherein said step of securing the suture retainer against movement relative to the suture includes heating at least a portion of material forming the suture retainer into a transition temperature range of the material of the suture retainer.

56. A method as set forth in claim 45 wherein the suture retainer has polymer chains oriented in a direction extending along a longitudinal axis of a portion of the suture, the polymer chains being contracted to cause material of the suture retainer to grip the suture.

57. A method comprising the steps of providing a flexible force transmitting member which is biodegradable and is formed by a plurality of interconnected strands which are at least partially formed of polylactide, positioning the flexible force transmitting member relative to body tissue, tensioning the flexible force transmitting member to transmit force from the strands of polylactide to the body tissue, and maintaining tension in the flexible force transmitting member by securing a biodegradable retainer which is at least partially formed of polylactide to the flexible force transmitting member, said step of securing a biodegradable retainer to the flexible force transmitting member includes bonding material of the retainer to the strands of polylactide, said step of bonding material of the retainer to the strands of polylactide includes heating at least a portion of the material of the retainer into a transition temperature range of the material of the retainer.

58. A method as set forth in claim 57 wherein first and second portions of the flexible force transmitting member extend through the retainer in a side-by-side relationship.

59. A method as set forth in claim 57 further including the step of inserting one end of the strands of polylactide through an opening in the retainer, said step of bonding material of the retainer to the strands of polylactide includes pressing material of the retainer which at least partially defines the opening in the retainer against the strands of polylactide.

60. A method as set forth in claim 57 wherein said step of bonding material of the retainer to the strands of polylactide includes gripping a first portion of the strands of polylactide with the retainer and gripping a second portion of the strands of polylactide with the retainer.

61. A method as set forth in claim 57 further including the step of pressing the strands of polylactide against the body tissue under the influence of tension in the flexible force transmitting member.

62. A method as set forth in claim 57 wherein the retainer has polymer chains oriented in a direction extending along a longitudinal axis of a portion of the force transmitting member, the polymer chains being contracted to cause the material of the retainer to grip the force transmitting member.

63. A method comprising the steps of providing a flexible force transmitting member which is at least partially formed of a plurality of strands of a biodegradable material, positioning the force transmitting member relative to body tissue with a longitudinal extending central portion of the strands of biodegradable material extending at least part way around the body tissue, providing a retainer formed of biodegradable material, tensioning the strands of biodegradable material to apply force against the body tissue with the central portion of the strands of biodegradable material, and maintaining the tension in the strands of biodegradable material by gripping a first portion of the strands of biodegradable material with the retainer at a location adjacent to a first end of the central portion of the strands of biodegradable material and by gripping a second portion of the strands of biodegradable material with the retainer at a location adjacent to a second end of the central portion of the strands of biodegradable material, the first and second portions of the strands of biodegradable material extend through the retainer in a side-by-side relationship.

64. A method as set forth in claim 63 wherein said steps of gripping a first portion of the strands of biodegradable material with the retainer and gripping a second portion of the strands of biodegradable material with the retainer includes heating material of the retainer into a transition temperature range of the material of the retainer and plastically deforming the heated material of the retainer.

65. A method as set forth in claim 63 wherein said step of gripping the second portion of the strands of biodegradable material with the retainer includes bonding material of the retainer to the second portion of the strands of biodegradable material.

66. A method as set forth in claim 63 further including the step of inserting one end of the strands of biodegradable material through an opening in the retainer, said step of gripping a second portion of the strands of biodegradable material with the retainer includes pressing material of the retainer which at least partially defines the opening in the retainer against the strands of biodegradable material.

67. A method as set forth in claim 63 wherein said steps of gripping a first portion of the strands of biodegradable material with the retainer and gripping a second portion of the strands of biodegradable material with the retainer includes contracting polymer chains which extend along the strands of biodegradable material.

68. A method comprising the steps of providing a flexible force transmitting member which is at least partially formed of a plurality of strands of a biodegradable material, positioning the force transmitting member relative to body tissue with a longitudinal extending central portion of the strands of biodegradable material extending at least part way around the body tissue, providing a retainer formed of biodegradable material, tensioning the strands of biodegradable material to apply force against the body tissue with the central portion of the strands of biodegradable material, and maintaining the tension in the strands of biodegradable material by gripping a first portion of the strands of biodegradable material with the retainer at a location adjacent to a first end of the central portion of the strands of biodegradable material and by gripping a second portion of the strands of biodegradable material with the retainer at a location adjacent to a second end of the central portion of the strands of biodegradable material, said steps of gripping a first portion of the strands of biodegradable material with the retainer and gripping a second portion of the strands of biodegradable material with the retainer includes heating material of the retainer into a transition temperature range of the material of the retainer and plastically deforming the heated material of the retainer.

69. A method as set forth in claim 68 wherein said steps of gripping a first portion of the strands of biodegradable material with the retainer and gripping the second portion of the strands of biodegradable material with the retainer includes bonding material of the retainer to the second portion of the strands of biodegradable material.

70. A method as set forth in claim 68 further including the step of inserting one end of the strands of biodegradable material through an opening in the retainer, said step of gripping a first portion of the strands of biodegradable material with the retainer and gripping a second portion of the strands of biodegradable material with the retainer includes pressing material of the retainer which at least partially defines the opening in the retainer against the second portion of the strands of biodegradable material.

71. A method as set forth in claim 68 wherein said steps of gripping a first portion of the strands of biodegradable material with the retainer and gripping a second portion of the strands of biodegradable material with the retainer includes contracting polymer chains which extend along the strands of biodegradable material.

72. A method as set forth in claim 68 wherein said step of plastically deforming heated material of the retainer includes pressing heated material of the retainer against one of the first and second portions of the strands of biodegradable material.

73. A method as set forth in claim 72 wherein said step of heating material of the retainer into the transition temperature range includes heating material of the retainer disposed adjacent to the one of the first and second portions of the strands of biodegradable material.

* * * * *